(12) United States Patent
Fleischer

(10) Patent No.: US 8,012,130 B2
(45) Date of Patent: *Sep. 6, 2011

(54) PLASTER DEVICE FOR SUPPORTING A BENDED LENGTH OF A TUBE

(75) Inventor: Philip Fleischer, Copenhagen S (DK)

(73) Assignee: Lina Medical ApS, Glostrup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/628,700

(22) Filed: Dec. 1, 2009

(65) Prior Publication Data
US 2010/0121280 A1    May 13, 2010

Related U.S. Application Data

(63) Continuation-in-part of application No. 11/518,568, filed on Sep. 8, 2006, now Pat. No. 7,648,485, which is a continuation-in-part of application No. PCT/EP2005/002677, filed on Mar. 14, 2005.

(30) Foreign Application Priority Data

Mar. 12, 2004 (DK) ................................ 2004 00406

(51) Int. Cl.
*A61M 5/32* (2006.01)
(52) U.S. Cl. ...................................................... 604/174
(58) Field of Classification Search .......... 604/174–180, 604/161, 164.01, 250
See application file for complete search history.

(56) References Cited

U.S. PATENT DOCUMENTS

| 2,669,231 | A | | 2/1954 | Fisher | 604/179 |
|---|---|---|---|---|---|
| 4,579,120 | A | | 4/1986 | MacGregor | 600/392 |
| 4,898,587 | A | * | 2/1990 | Mera | 604/174 |
| 5,073,170 | A | * | 12/1991 | Schneider | 604/180 |
| 5,224,935 | A | | 7/1993 | Hollands | 604/180 |
| 5,616,131 | A | | 4/1997 | Sauer et al. | 604/174 |
| 5,637,098 | A | | 6/1997 | Bierman | 604/180 |
| 5,685,859 | A | | 11/1997 | Kornerup | 604/180 |
| 5,941,856 | A | | 8/1999 | Kovacs et al. | 604/179 |
| 6,375,639 | B1 | | 4/2002 | Duplessie et al. | 604/174 |
| 6,565,537 | B2 | * | 5/2003 | Tollini | 604/174 |
| 7,547,296 | B2 | | 6/2009 | Lampropoulos et al. | 604/180 |

FOREIGN PATENT DOCUMENTS

| EP | 0 463 718 A1 | 1/1992 |
|---|---|---|
| WO | WO 95/33508 A1 | 12/1995 |
| WO | WO 98/10823 A1 | 3/1998 |

\* cited by examiner

*Primary Examiner* — Matthew F Desanto
(74) *Attorney, Agent, or Firm* — Winston & Strawn LLP

(57) ABSTRACT

A plaster device serves for fixating a length of a medical tube in relation to a skin surface of an individual having the tube inserted into a body part via an opening. The plaster device has an adhesive part having an upper side, an adherent lower side for attaching the plaster device to the skin, a through-opening for receiving the tube, a support part at least partly attached to the upper side of the adhesive part and arranged for supporting a bent length of the inserted tube, and a fastener for securing the tube on the support part. The support part is an integral unit having a branched-off portion defining at least one recess for accommodating at least a part of the fastener, preferably a fastener that is elastic. A frictional force between the tube and the fastener guarantees that the tube is prevented from moving or displacing to the patient's discomfort. The convex shape of the upper supporting surface provides a smooth anti-kinking support and guidance for the bended tube.

21 Claims, 10 Drawing Sheets

PLASTER DEVICE FOR SUPPORTING A BENDED LENGTH OF A TUBE

CROSS-REFERENCE TO RELATED APPLICATIONS

Figure 1:
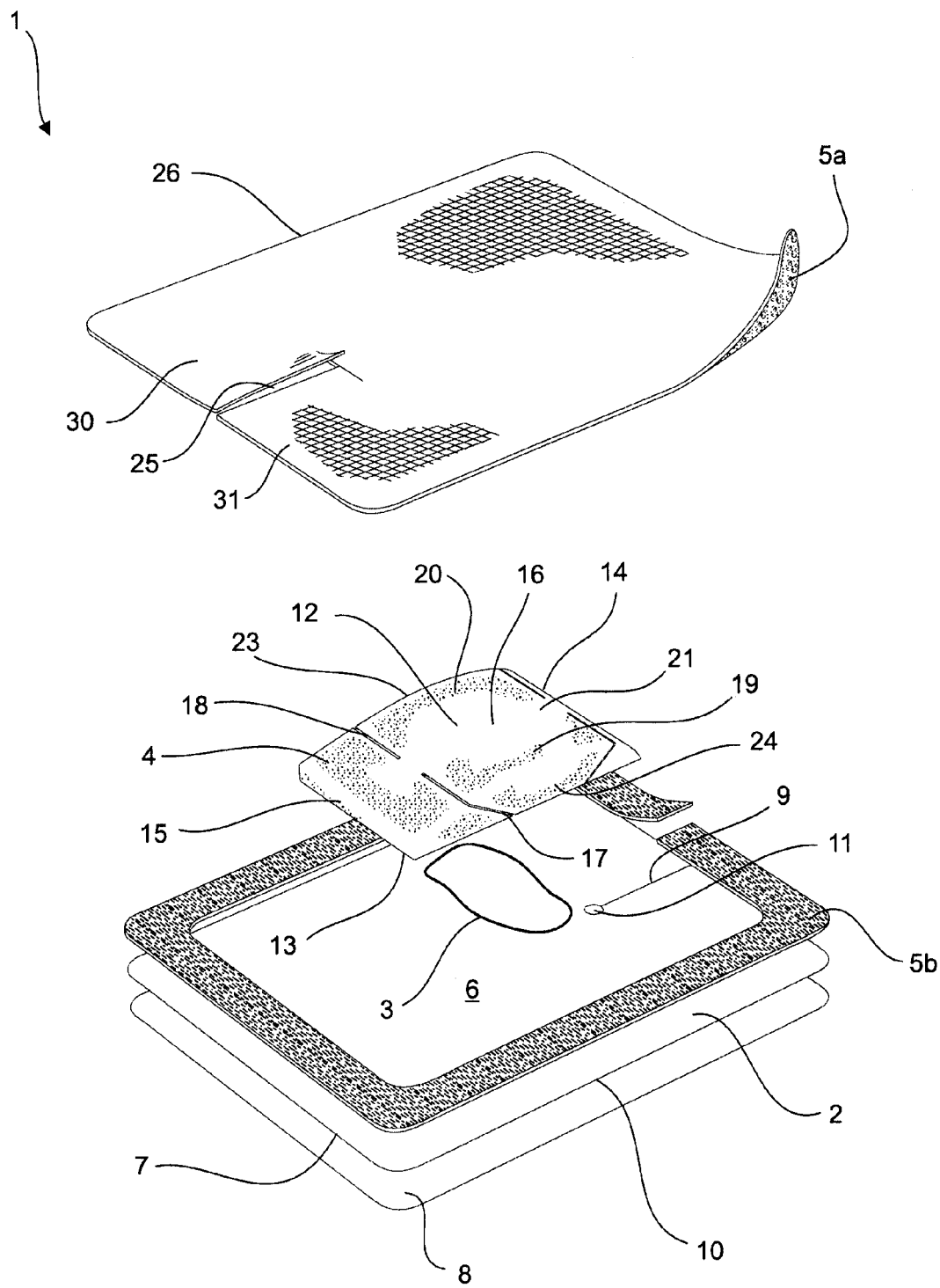

This application is a continuation-in-part of application Ser. No. 11/518,568 filed Sep. 8, 2006, now U.S. Pat. No. 7,648,485, which in turn is a continuation-in-part of International application no. PCT/EP2005/002677 filed Mar. 14, 2005. The entire content of each prior application is expressly incorporated herein by reference thereto.

BACKGROUND

The present invention relates to a plaster device for fixating a length of a medical tube in relation to a skin surface of a patient having said tube inserted into a body part via an opening in the skin surface.

The plaster device is of the kind including an adhesive part having an upper side, an adherent lower side for attaching the plaster device to the skin surface, and a through-opening for receiving the tube, a support part partly attached to the upper side of the adhesive part and arranged for supporting a bent length of said inserted tube, and fastenings means for securing the tube on the support part.

Medical tubes are often introduced into a wound, a cavity or an organ of a human or animal body to facilitate sustained drainage or sustained supply of liquid or gaseous substances.

Examples of medical tubes used for drainage include, but are not limited to, a chest drainage tube, a lumpectomy or a mastectomy drainage tube, a renal drainage tube for use in e.g. dialysis or percutaneous nephrostomy, and a drainage tube for emptying e.g. an encystment or an abscess.

Examples of medical tubes used for supplying a substance to the patient include, but are not limited to, tubes and catheters for controlled administration of palliatives, such as analgesia, and hormones, such as insulin, delivered via e.g. an insulin pump.

Proper securing of the medical tube at and in relation to the patient's skin is necessary to improve the patient's comfort during the treatment. It is of outmost importance to avoid contamination of the puncture site, to avoid dislodgement of the tube, e.g. during inspection of the puncture site or during the patient moving, and to avoid kinking, blocking or obstruction of the tube to prevent discontinuity of drainage or supply.

Traditionally, a medical tube, inserted into the patient through an incision in the skin, is fixated by means of sutures at the incision site. Such sutures leaves scars and may even serve as wicks for undesirable contamination of the incision and the skin around the incision site. To prevent such contamination and to improve securing of the tube, a plaster strapping can be attached to both the skin and around the tube adjacent the incision.

Several approaches have been made to improve this securing technique, which is very distressing to the patient. Nowadays, more sophisticated techniques are used due to improved plaster devices and skin-friendly adhesives.

An improved catheter retainer has been suggested in British patent document GB 2,288,530. The retainer can be adhesively secured to a patient's skin at the incision site to hold an introduced catheter in a fixed position. The retainer allows the catheter to be bent through a right angle as the catheter exits the patient without it kinking The catheter is kept in place in the bent position in a slot by means of a clamp, which compresses and clamps the catheter into the slot. This device has uncomfortable rigid parts protruding from the patient's skin and the patient's clothes may be caught on the clamp, which accordingly will release the catheter. Another disadvantage is that it is impossible to inspect the incision site and consequently it is impossible to obtain information regarding infection at the site and/or leakage through the incision.

A plaster device without any substantially rigid parts is known from International patent application WO 95/33508. This known device has a plaster component for attaching the device to the skin of the patient and a support component for supporting a tube inserted into the patient's body via an incision in the skin. The tube is supported on the support component such that the tube changes orientation from an orientation substantially perpendicular to the patient's skin to an orientation substantially parallel to the patient's skin. The tube is fixated in this bent use-position by means of an adhesive securing strip applied sealingly over the tube and the support component. It is possible to inspect the tube and the site of the incision if the securing strip is transparent. However, it is impossible to obtain a reliable and convincing overview of the condition around the entire site of incision without removing the securing strip. Since the tube is not sutured to the incision site it is difficult to ensure that the tube is not displaced during removal of the adhesive securing strip. Consequently, this manipulation of the securing strip may displace the tube resulting in discomfort for the patient. In addition, the tube is covered with adhesive residues and will inadvertently stick to any adjacent component. Due to this disadvantage, the nurse is not inclined to perform as many inspections as are needed in order to be completely sure that e.g. no bleeding, infection or allergic reaction appears around the incision site, a part of which is hidden by the bent tube.

This prior art document further discloses an alternative embodiment proposing a securing strap or tie for fixating the tube in the use-position. The support part of this embodiment consists of three individual elements: two side elements of a soft foamed material attached on each side of a central element of a hard or rigid foamed material. A groove serving for preventing displacement of the tube is defined by the upper side of the central element and the sides of the side elements adjacent the central element. The combined support part is attached to the underlying plaster component so that the securing strap is arranged around the central element. This structure has the disadvantage that during tightening of the strap, there is a risk that the central element will be detached from any of the elements surrounding it and as a consequence destroy the entire structure. Since the bent tube is situated in the groove the tie strap is only provided for keeping the tube down in the groove and cannot prevent the tube from moving in the lengthwise direction of the support part. Also the free end of the securing strap is provided with barbs to in an awkward and inconvenient manner non-releaseably locking with an eye provided on the opposite end of the tie to create a locking loop. Just as a cable tie the created loop needs to be cut to gain access to the cables/tube that are held in place by the tie/strap. Another disadvantage of the strap of the device disclosed in WO 95/33508 is that once the free end of the tie strap is passed through the eye this free end sticks out at the risk of getting caught and withdrawn from the plaster thereby pulling the tube out of the groove and eventually out of the incision and body cavity into which the tube is inserted. If the free end is cut off only the barbs hold the strap closed which may be insufficient to resist exterior force applied to the strap when the patient moves around.

From European patent EP 0 463 718 B1 is known a catheter retainer as a means to avoid stitching of the catheter to the skin of the wearer. EP 0 463 718 B1 discloses a plaster device having protruding ears. The catheter is exteriorised between said ears and at a very short section the catheter is secured to the ears by means of a thread. The thread is wound around both the ears and the catheter using a number of winds to make sure that the catheter is not displaced when the patient moves. The use of this known device includes a considerable risk that the thread gets tangled up during winding and as a result the thread is complicated to unwind. Moreover, when arranging the thread around the catheter care must be taken not to clamp the catheter together. To avoid this often a rather loose winding is applied to the catheter resulting in that the catheter can slide back and forth with great discomfort to the patient as a result. Moreover this known device does not provide support for a bent length of a tube.

Accordingly, there is a need for improved plaster devices to overcome the deficiencies of the prior art, and these are now provided by the present invention.

SUMMARY OF THE INVENTION

It is a first aspect according to the present invention to provide a simple and inexpensive plaster device for improved fixation on a patient's skin of a medical drainage or supply tube.

It is a second aspect according to the present invention to provide a plaster device for fixating a medical drainage or supply tube on a patient's skin in a use-position, in which kinking, blocking, compressing or obstruction of the tube is prevented.

It is a third aspect according to the present invention to provide a plaster device, which is easy to apply and use, and provides a comfortable and convenient fixation of a medical drainage or supply tube on a patient's skin.

It is a fourth aspect according to the present invention to provide a plaster device, which does not get caught in the surroundings, e.g. the patient's clothes.

It is a fifth aspect according to the present invention to provide a plaster device for preventing a medical drainage or supply tube inserted through a patient's skin from displacing after fixation and during movement of the patient.

The novel and unique features whereby the above and further aspects are obtained is the fact that the support part is an integral unit comprising a central part, the central part is a pivotably fastening flap for attaching the fastening means, and said fastening flap protrudes towards a free end between a front-end part of the support part and a rear-end part of the support part crosswise an axis of the support part along which the bent length of the inserted tube extends when supported.

The support part is an integral unit having a branched-off portion in the form of a simple cleat having only one arm, which arm is defined by at least one recess in the support part, which at least one recess serves for accommodating at least a part of the fastening means.

As used herein the term "cleat" or "cleat-shaped" is to be understood as an element having a shape and function substantially similar to a cleat on e.g. a boat. In the context of the present application "cleat" or "cleat-shaped" therefore means an element having a protruding portion around which a fastening means can be twisted for securing an object.

By designing the support part as an integral unit, the risk of the support part falling apart during fastening of the tube with the fastening means, is eliminated. The at least one recess branches off the fastening flap from the support part to create a hinge or pivot constituted by the remaining attachment of the fastening flap to the support. In this embodiment the recess is substantially U-shaped. Thus the recess may be interpreted as one single U-shaped recess or be seen as two opposite recesses crossing the axis of the support part along which the bent length of the tube extends, which recess or opposite two recesses parts the fastening flap from the support part. Accordingly the fastening flap pivots between the front-end part and the rear-end part as an integral part of the support part and of sufficient size and shape for supporting the bent length of the tube.

In an expedient embodiment the pivotable fastening flap can be parted from the support part simply by means of slots or incisions extending crosswise a longitudinal axis of the support part from a first side of the support part and a distance towards a second side of the support part opposite the first side.

In this simple embodiment of a plaster device according to the present invention the slots or incisions constitutes a recess that provides accommodation space for the fastening means, and establishes a hinge for pivoting the fastening flap away when arranging the fastening means on the fastening flap. The incisions or slots can be parallel, converge, diverge or have different orientations from the first side towards the opposite second side. Incisions can be made simply by cutting from a first side of a unit blank body for the support part and inside the unit blank body a distance towards the second side. The first and second sides can be parallel to the longitudinal axis of the support part, but curved first and second sides are intended within the scope of the present invention due to other intended shapes of the support part. The support part can for example be shaped as a cap part of a sphere, an ellipsoid or a paraboloid or combinations or parts of these and other shapes. By providing slots or incisions only extending a part of the crosswise distance of the support part an expedient and simple hinge for pivoting the fastening flap can be obtained.

Another way of providing a support part with a pivotable fastening part is to make the slots during a moulding operation step of the integral support part structure with pivotable fastening flap.

Advantageously, the fastening flap has a first face for supporting the bent length of the inserted tube, and an opposite second face, said second face has an attachment means for attaching at least a first part of the fastening means, so that the fastening means does not get detached from the support part when manipulated during firmly securing the bent length of the tube on top of the support part by means of said fastening means. Since only a first part of the fastening means is accommodated between the fastening flap and the adhesive part before the fastening means is secured to the bent length of the tube, a second part of the fastening means is free and accessible to be easily grasped by a user, e.g. by means of the users fingers.

Preferably the attachment means can be a groove made in the second face of the fastening flap. The groove can have any shape that suffices for keeping the fastening means firmly together with the attachment means. The attachment means can for example also be a tongue, flap or hook partly cut out of the fastening flap goods at the second face of the fastening flap. The groove may extend the whole way across the second face of the fastening flap or just over a part of the second face of the fastening flap. The attachments means can also be constituted by indentations or small slits at the pivot point for the hinge between the fastening flap and the support part, thus at the hinge points where the support part splits into the fastening flap, the front-end part and the rear-end part.

In the preferred embodiment the fastening means is made of elastic, flexible, resilient or springy material, preferably having a memory, the fastening means is easy and expeditious to apply around the tube for carefully fastening the tube against the support part without compression of the tube's lumen. A simple loop, ring, band or strap of rubber, silicone or polyurethane has been found especially fit for use, but other kinds of loops, rings, straps, bands or laces can also be used. For the comfort of the patient it is preferred that the material of the fastening means is selected so that the frictional force between the material of the tube and the material of the fastening means is sufficiently high to prevent mutual dislocation or displacement of the fastening means and the tube in relation to each other.

Prior art devices for similar purposes have no fastening means, which in a similar simple reliable manner can provide friction to prevent displacement.

If the fastening means is detachably arranged in relation to the support part and the adhesive part, the fastening means can easily be substituted with a new fastening means without having to change the entire plaster device.

Although it is preferred that the fastening means is detachable, it is obvious to the skilled person that a part of the fastening means used in the present invention can quite as well be permanently attached to a part of the plaster device, in particular to the attachments means.

To be able to better catch hold of the fastening flap, said fastening flap can have a free end provided with a free grasping flap.

If an area of the upper side of the adhesive part between the front-end part and the rear-end part of the support part has a first engaging means and the second face of the fastening flap has a second engaging means for releasable engaging the first engagement means the fastening flap can be snap-fastened to the subjacent adhesive part once the bend length of the tube has been fastened to the fastening flap, to bring the tube as close as possible to a convenient non-protruding bent configuration in proximity with the part of the patient wherefrom the tube protrudes. The engaged first and second engagement means thus serves for keeping the fastening means close to the patient's body while the pivotability of the fastening flap facilitates easy application of the fastening means.

In an embodiment where at least an area of the support part supporting the bent length of the tube has a retainer means for retaining the tube, said tube can be held in place on top of support part without substantially no additional use of the fingers while the fastenings means is secured around the fastening flap. Because the fastening means is secured around the fastening flap it may be preferred that it is the fastening flap that has the retainer means, which retainer means for example could be an adhesive or slightly sticky area on the first face of the fastening flap.

The support part may have an elongated configuration with a substantially convexly curved upper supporting surface for supporting the tube in the use-position, however other shapes are contemplated within the scope of the present invention. The upper supporting surface includes the first face of the fastening flap and constitutes an advantageous smooth supporting surface for, in an anti-kinking manner, supporting the length of the tube bent through a right angle.

It is preferred that the support part is made of a foamed material, which is substantially dimensionally stable, so that the support part substantially will keep its shape when the plaster device is used, and is so flexible that it will yield without compressing the supported tube if the patient bumps or presses against something.

Moreover, the recesses constitute a simple means for accommodating the detachable fastening means used for lashing or anchoring the tube into a secured relationship with the supporting surface of the support part, in particular the first face of the fastening flap. Once the tube is secured with the fastening means, movement or displacement of the tube is prevented because the fastening means surrounding the pivotable arm constituted by the fastening flap will keep the tube secured in a flexible and frictionally manner.

A further advantage exists in that the fastening means can easily be loosened and disengaged from the attachment means of the fastening flap. No adhesive needs be involved for securing the fastening means on the support part. The tube may, if needed or desired, be carefully lifted so that areas otherwise not inspectable, such as e.g. the part of the incision site hidden by the bent tube and the support part, can be inspected and treated sufficiently early to prevent damages.

If occasion should render it necessary and appropriate, the tube may even be substituted by a new tube without change of the plaster device in use. No strong physical adherence exists between the inserted tube and the fastening means and the securing capability is not lost or reduced by simply detaching the fastening means as with the prior art devices.

In various embodiments a cleat-shaped portion can be more or less protruding to accommodate various types of fastening means thicknesses and the outer shape may also within the scope of the present invention be given any configuration generally having a stem and a head, e.g. a mushroom-like configuration. The length of the stem is decisive for providing a securing space recess of a certain size. A too long stem would tilt and does not provide any clamping effect. A too short stem leaves no room for the fastening means and makes it very difficult to place the fastening means correctly. In the simple embodiment with a fastening flap the stem is provided by means of the pivotable fastening flap arm.

The plaster device may further comprises a cover means for covering at least a part of the bent length of the tube at least in the vicinity of the through-opening for protection of the inserted tube, which rests secured on the support part of the plaster device.

In a preferred embodiment the cover means includes a first cover part arranged for coupling together with either a second cover part attached to at least a section of the upper side of the adhesive part or for coupling to the adhesive part itself. The risk of infection is considerably reduced because the first and second cover parts when joined together enclose either the entire support part or at the part of the support part in the vicinity of the through-opening and the incision site where infection is most likely to happen.

In a very simple preferred embodiment the first cover part is a sheet of textile, preferably entirely made of a Velcro® hook and loop fastener or made of a textile having a Velcro® hook and loop fastener strip provided along the perimeter. The sheet must have an area sufficiently large to cover at least the support part in the use position. It is preferred that the textile is air permeable so that humidity is allowed to evaporate and humidification is avoided.

The VELCRO® sheet is preferably fully detachable but can alternatively be connected to any portion of the adhesive part e.g. an edge or a rim. The Velcro® sheet may have a smooth outside so that the plaster device not does catch the patient's clothes or other surrounding protruding elements.

The second cover part for coupling together with the first cover part can be a circumferential VELCRO® hook and loop fastener strip attached to the upper side of the adhesive part along or a distance from the perimeter of this, and arranged for sticking to the first cover part. A preferred distance between the perimeter of the adhesive part and the outline of the second cover part could for example be between 1-25 mm depending on the size of the adhesive part.

In a preferred embodiment according to the present invention the first cover part is smaller than the adhesive part, in which case the perimeter of the first cover part is coupled to the second cover part or the adhesive part at a distance from the perimeter of the adhesive part. This arrangement prevents the adhesive on the adhesive part to work loose its firm adhesive grip on the skin when the first cover part is move and manipulated during movement of the wearer.

For some purposes it is alternatively preferred that either the side of the rim portion of the first cover part facing the adhesive part or the rim portion of the upper side of the adhesive part itself or both these portions may be glued in order to stick sealingly together.

In an alternative embodiment the cover means can be an adhesive film or part of an adhesive film secured, attached or connected to the adhesive part in front of or close to the through-opening, making the cover means simple to apply on an appropriate part of the support part and bent length of the tube. In order to be able to inspect the incision site without having to remove the cover means the cover means can be transparent. Moreover, in this simple embodiment the adhesive film may extend at least partly over the fastening flap in use, so the adhesive film contributes to keeping the fastening flap in contact with the adhesive part, thus also contributes to hold the first and second engagement means in engaging relationship by keeping said engagement means towards each other.

The plaster device may also comprise at least one of the means selected from the group including absorbent agents or bactericides.

Absorbing layers may additionally be added to the structure or inserted where needed. Absorbing layers may include, as the absorbent agent, a hydrocolloid, for further ensuring that the incision site is kept dry. Also pads or compositions including e.g. a bactericide, an antibiotic and/or an antifungal agent for killing any active bacteria or fungus may be included in the structure. Also a medicament can be included in the structure. The absorbent layers or pads may be of any convenient material known to the person skilled in the art, e.g. cellulose webs, porous pads, non-wovens etc.

To prevent the adherent lower side of the adhesive part for attaching the plaster device to the skin from unintentionally sticking to other surface as well as to a suitable packaging the adhesive lower side may be protected by at least one release liner. Also an adhesive cover may be protected by a release liner in order not to get in the way while the fastenings means is arranged around the tube on the fastening flap.

The invention also relates to a method of applying the plaster device described and discussed above.

The method comprising the steps of applying the plaster device on the subject or user with the tube in proximity to the front-end part of the support part, bending the tube in supported relationship on the support part, and folding the second part of the fastening means over the bended length of the tube and securing the second end of the fastening means on the second face of the fastening flap.

However, to ensure that the bent length of the tube keeps in turned relationship substantially parallel to the skin surface onto which the plaster device is applied it may be beneficial to mate the first and second engagement means to keep said first and second engagement means stuck together. For example the first and second engagement means made be made as Velcro® hook and loop fasteners. Once the first and second engagement means have been engaged the height of the protruding support part is minimised to the convenience of the patient.

The position of the tube is fixed in that the tube is secured to the fastening flap. The tube cannot move in relation to the incision or puncture site or be displaced in or out at the body cavity due to the fastening means which has been secured around the tube and the fastening flap, which fastening means subsequently is brought into engaging contact with the adhesive part to clamp and hide both the first and the second part of the fastening means underneath the fastening flap away from the first face while carefully holding the tube secured at the support part.

Preferably the cover means can be applied to at least cover the bent length of the tube in proximity of the through-opening, however other degrees of coverage and areas to be covered are understood to be within the scope of the present invention.

BRIEF DESCRIPTION OF THE DRAWING FIGURES

Figure 2:
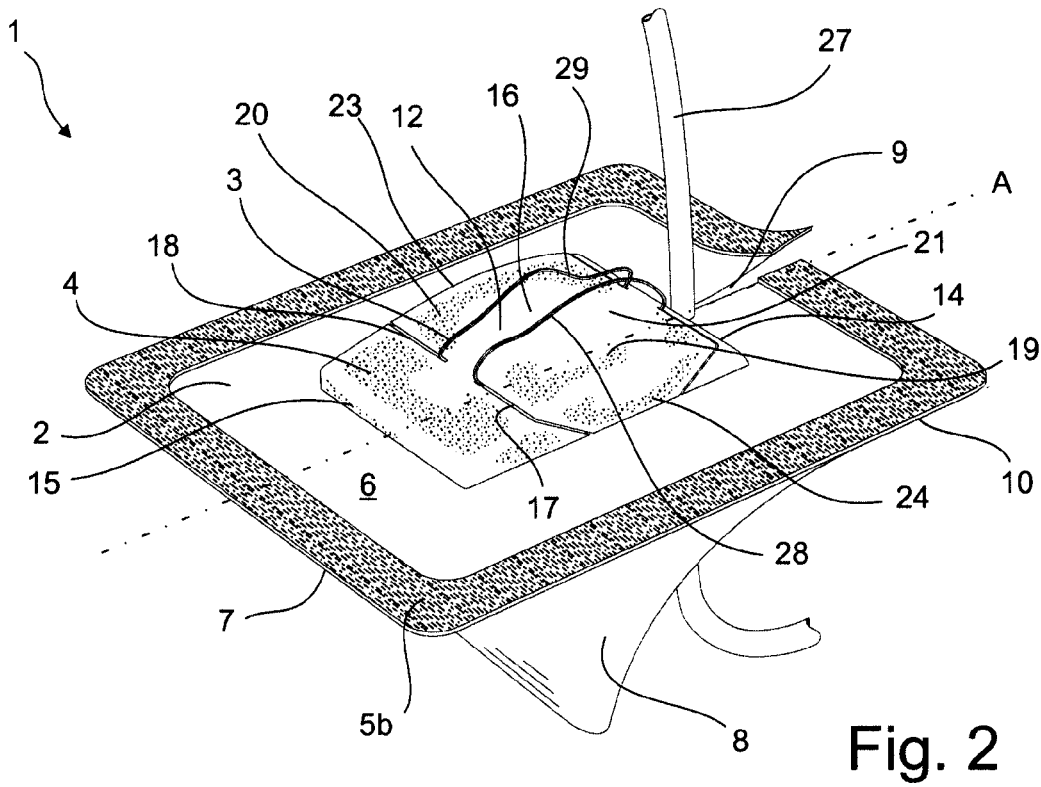
Figure 3:
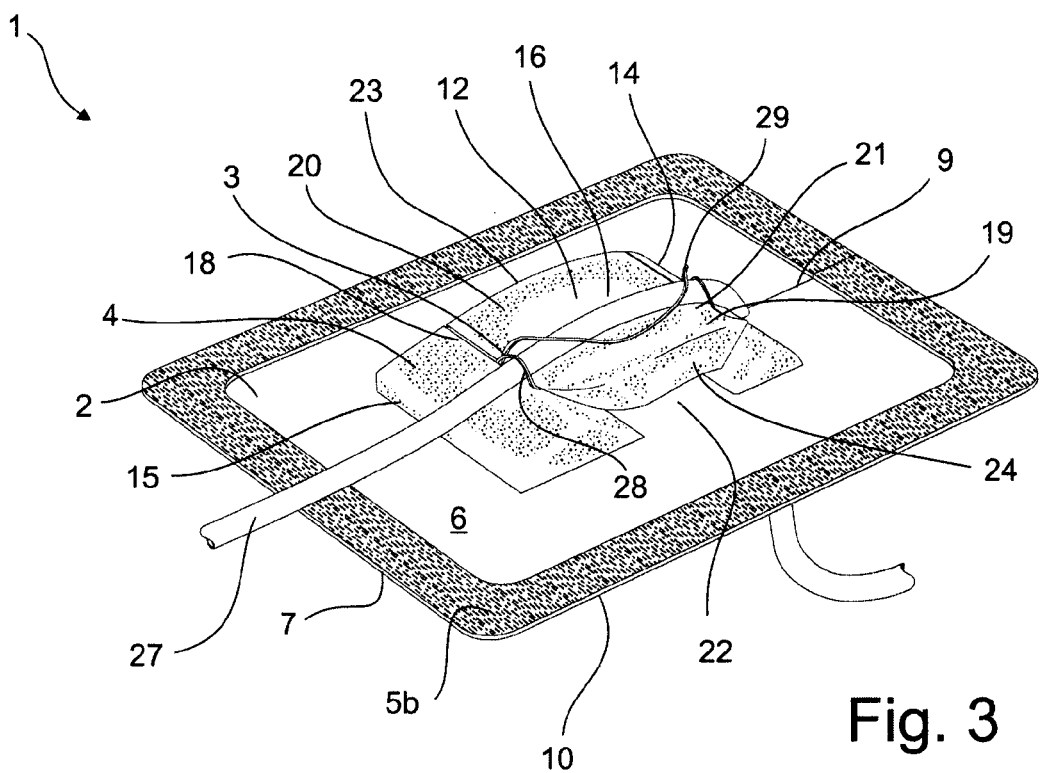
Figure 4:
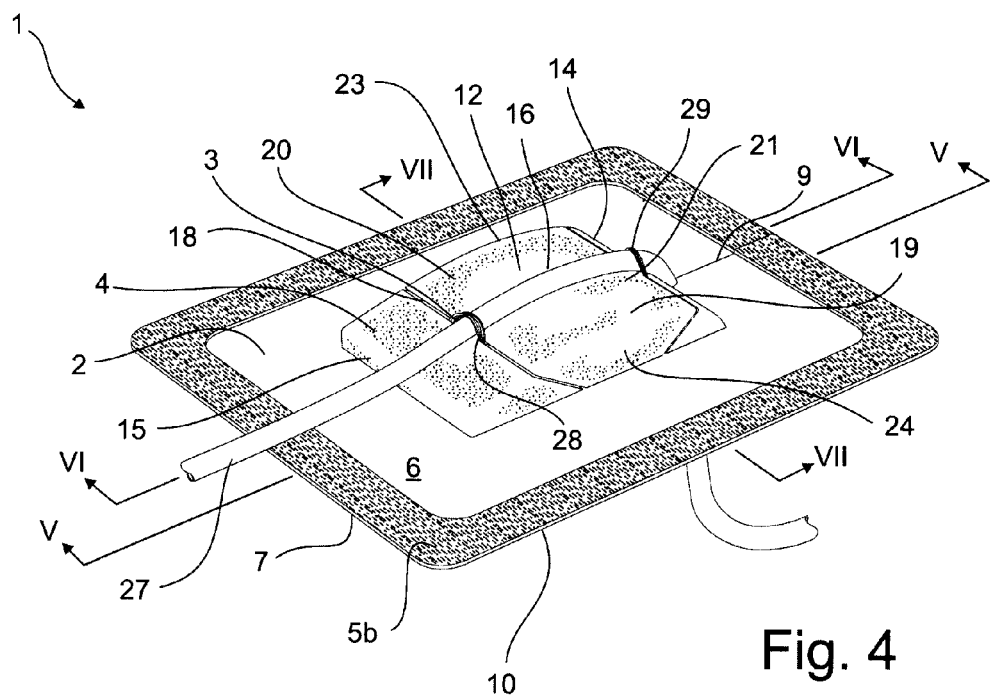
Figure 5:
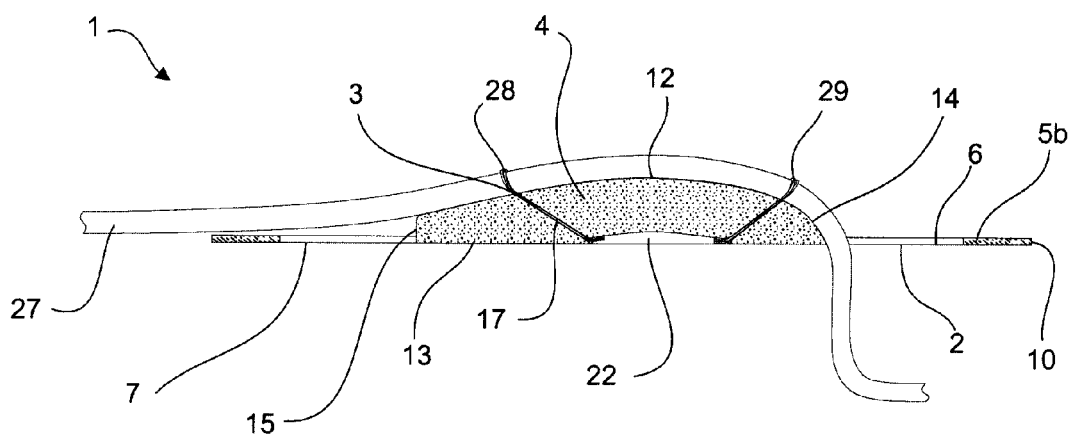
Figure 6:
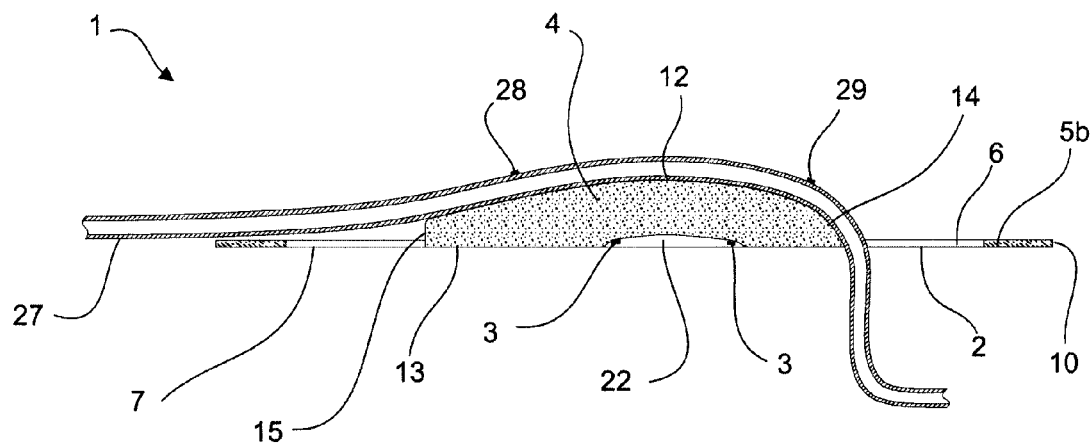
Figure 7:
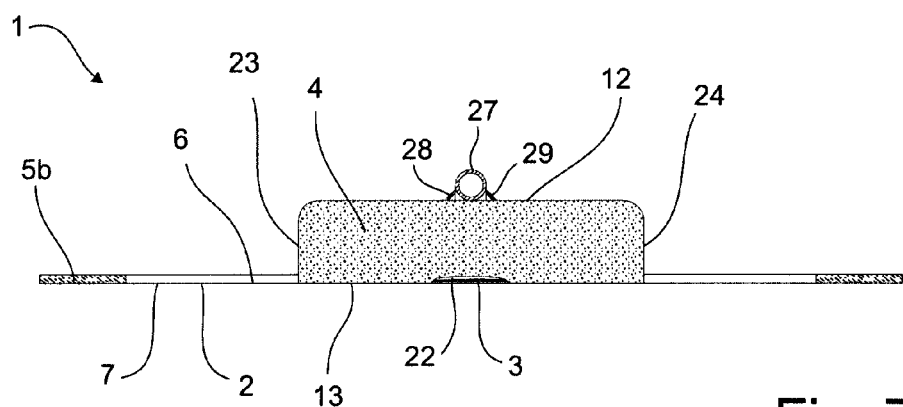
Figure 8:
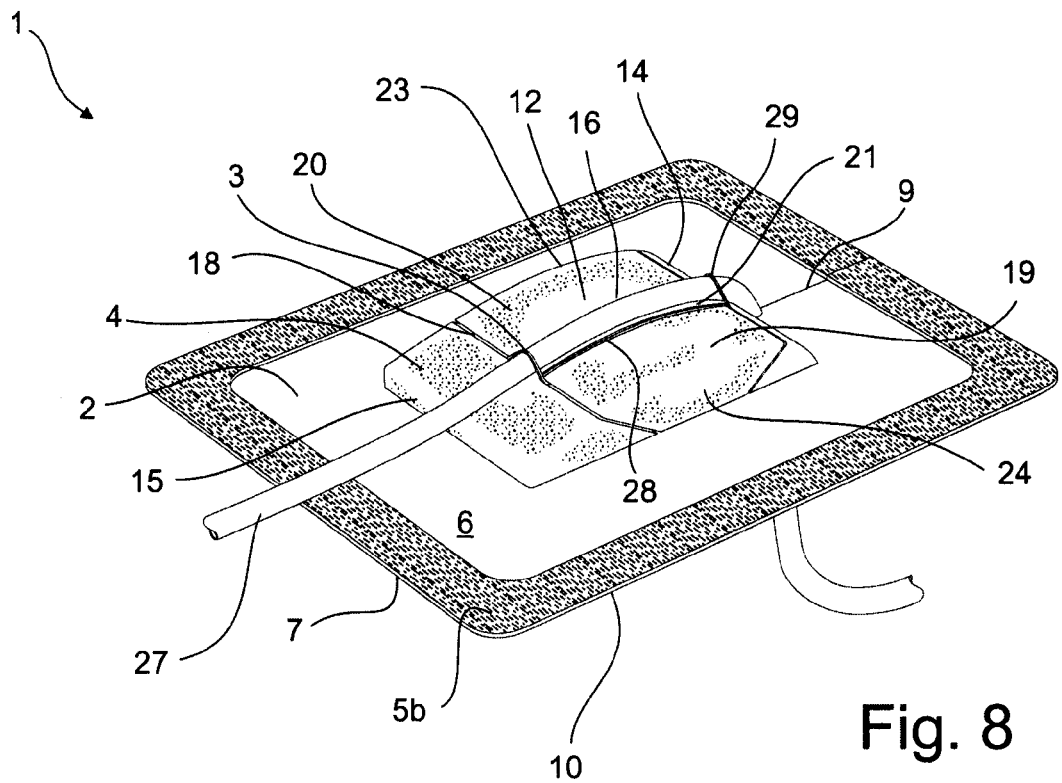
Figure 9:
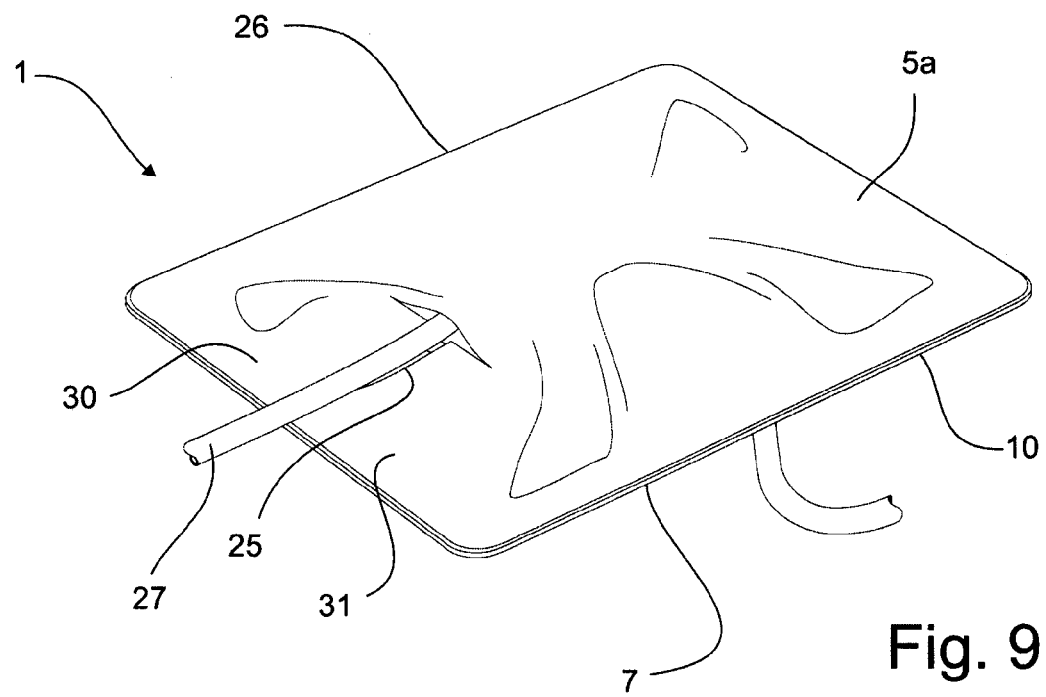
Figure 10:
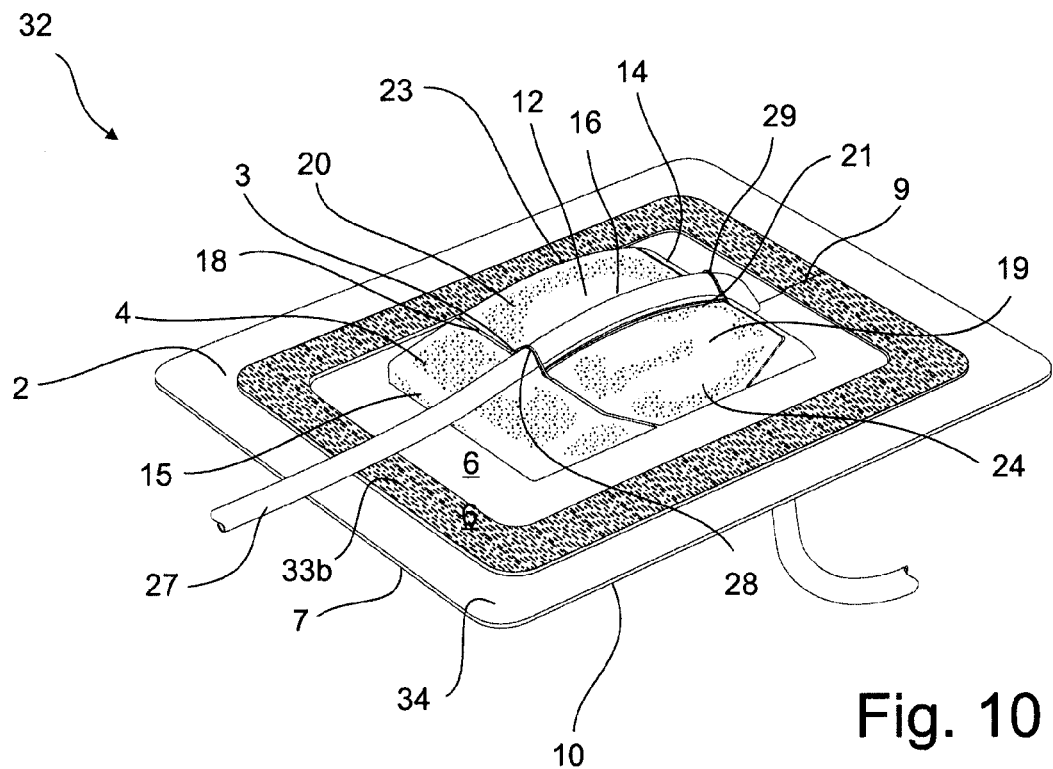
Figure 11:
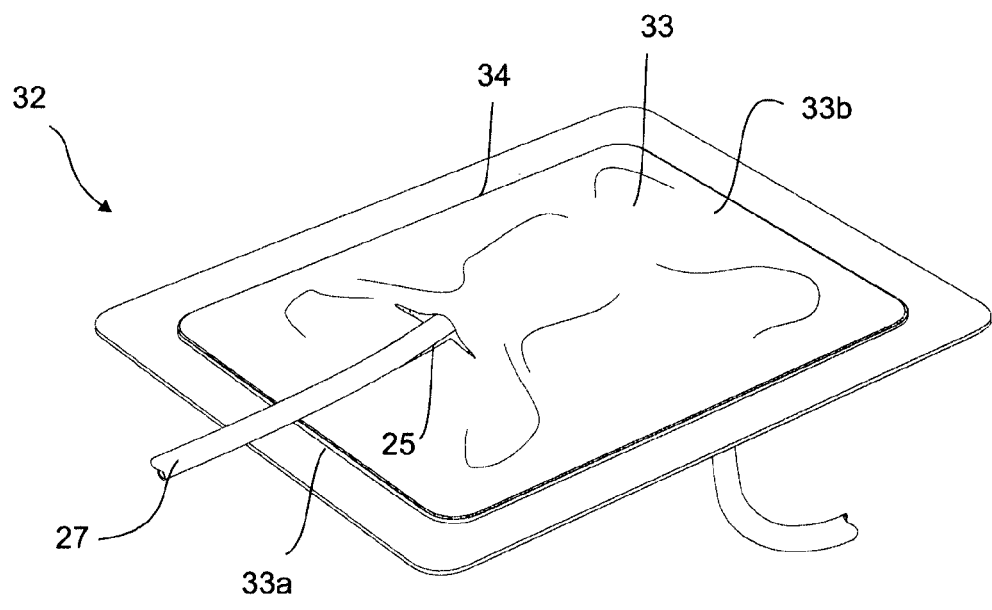
Figure 12:
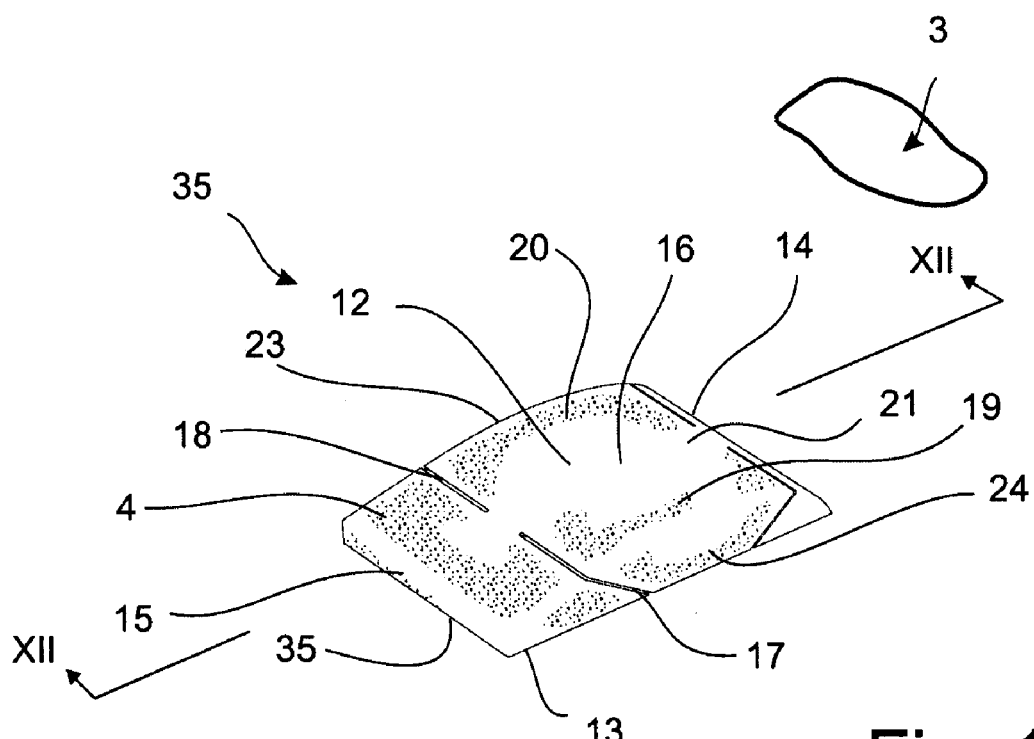
Figure 13:
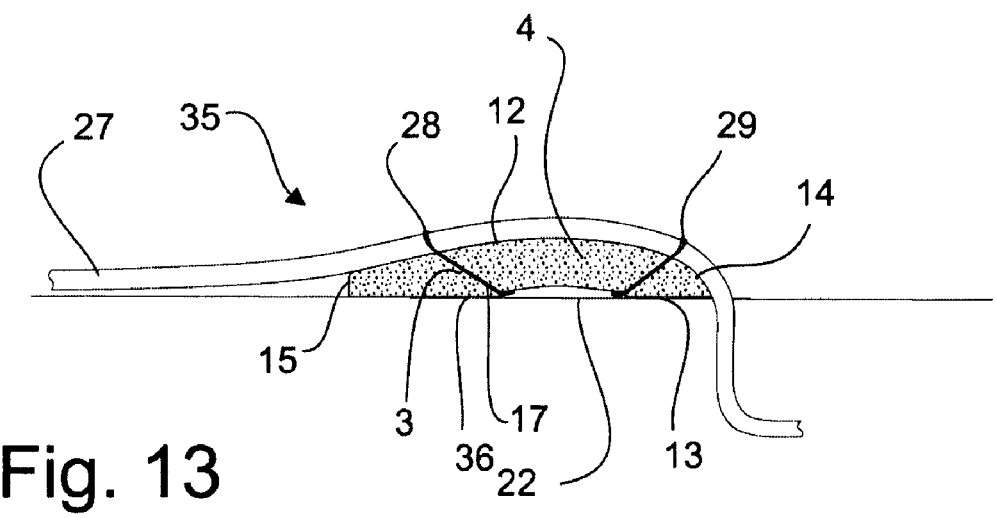

The invention will be further described below with reference to the drawings showing examples of embodiments for a plaster device according to the present invention, in which FIG. 1 is an exploded view of the elements of a first embodiment of a plaster device according to the present invention, FIG. 2 schematically shows the plaster device in FIG. 1 applied on a skin surface in relation to an inserted tube at a first step of the fixation procedure before the tube is fixated on the support part, FIG. 3 shows schematically a second step of the fixation procedure, in which the tube is bent through a right angle and partly fixated on the support part, FIG. 4 shows a third step of the fixation procedure, in which the fastenings means is fully fastened around the tube, FIG. 5 shows a longitudinal section along the line V-V in FIG. 4, FIG. 6 shows a longitudinal section along the line VI-VI in FIG. 4, FIG. 7 shows a cross-section along the line VII-VII in FIG. 4, FIG. 8 shows an alternative way of application of the fastening means around the tube, FIG. 9 shows a fourth step of the fixation procedure in which the first cover part is coupled to the second cover part for enclosing the bent length of the tube, FIG. 10 shows a perspective view of a second embodiment of a plaster device according to the present invention, FIG. 11 shows the second embodiment covered with a cover means, FIG. 12 shows a perspective view of a third, very simple embodiment of a plaster device according to the present invention, FIG. 13 shows a cross-section along the line XII-XII of the plaster device shown in FIG. 12 in use-position with a bent length of a tube.

Figure 14:
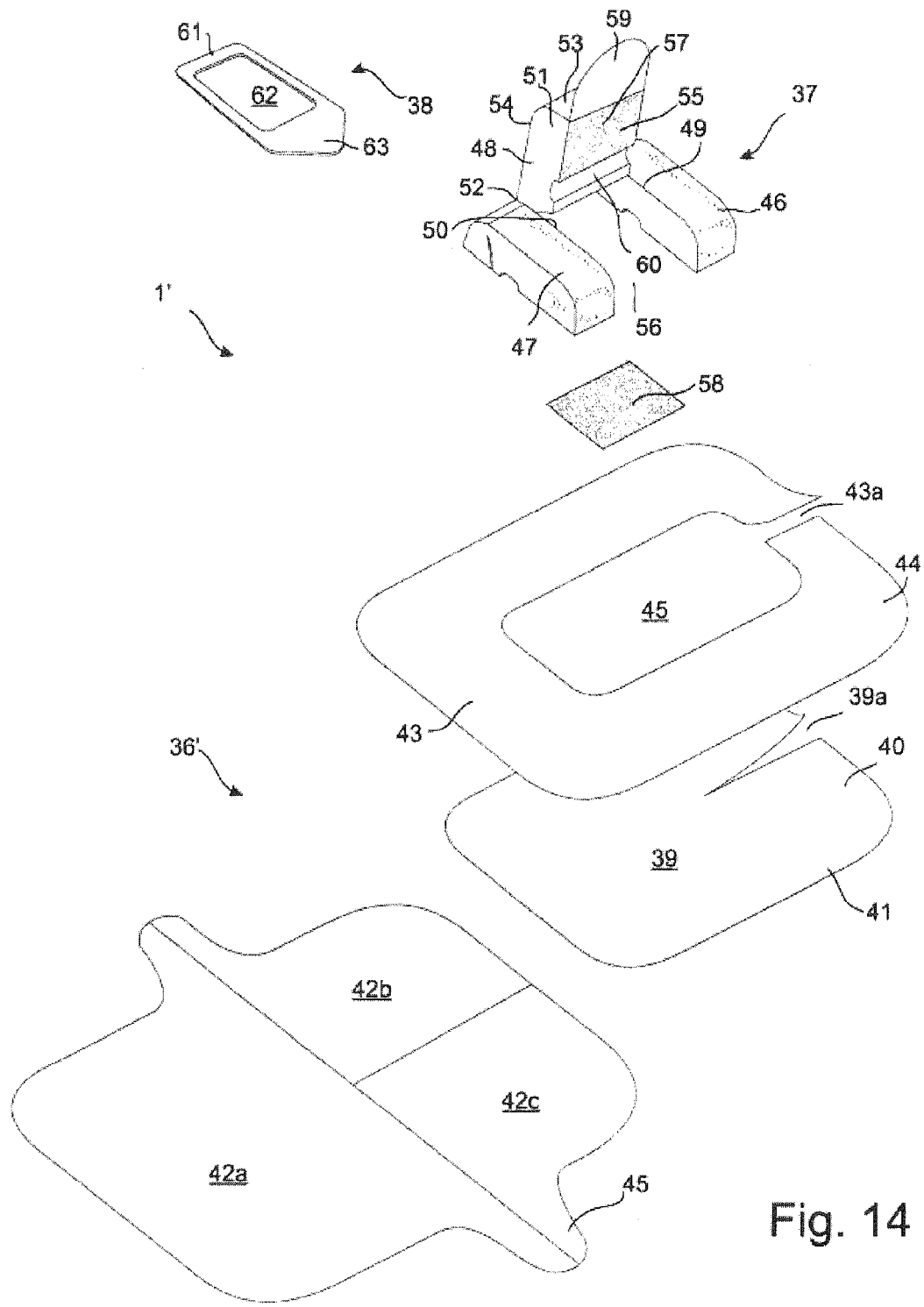
Figure 15:
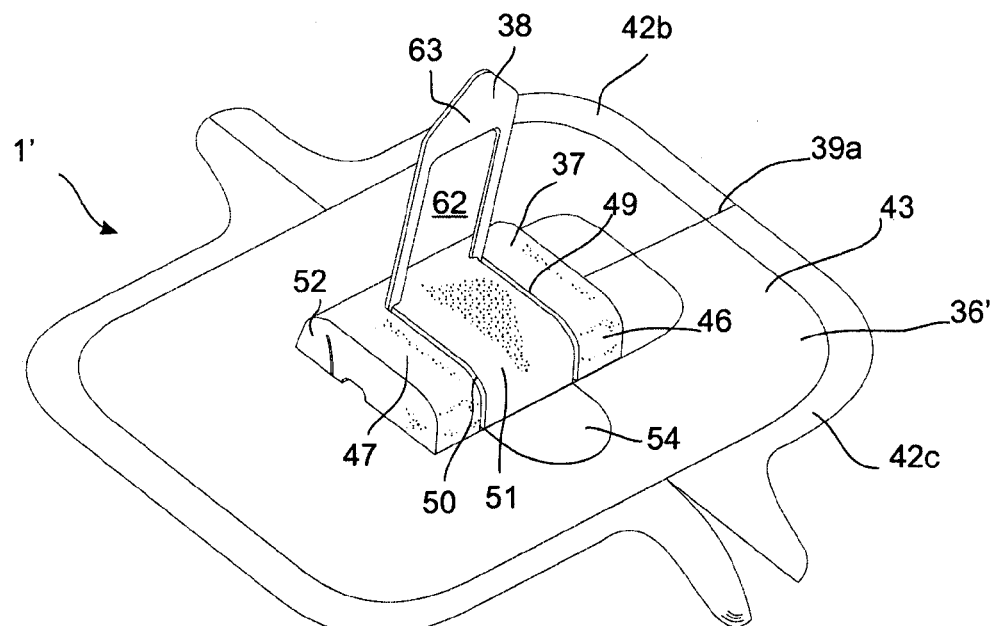
Figure 16:
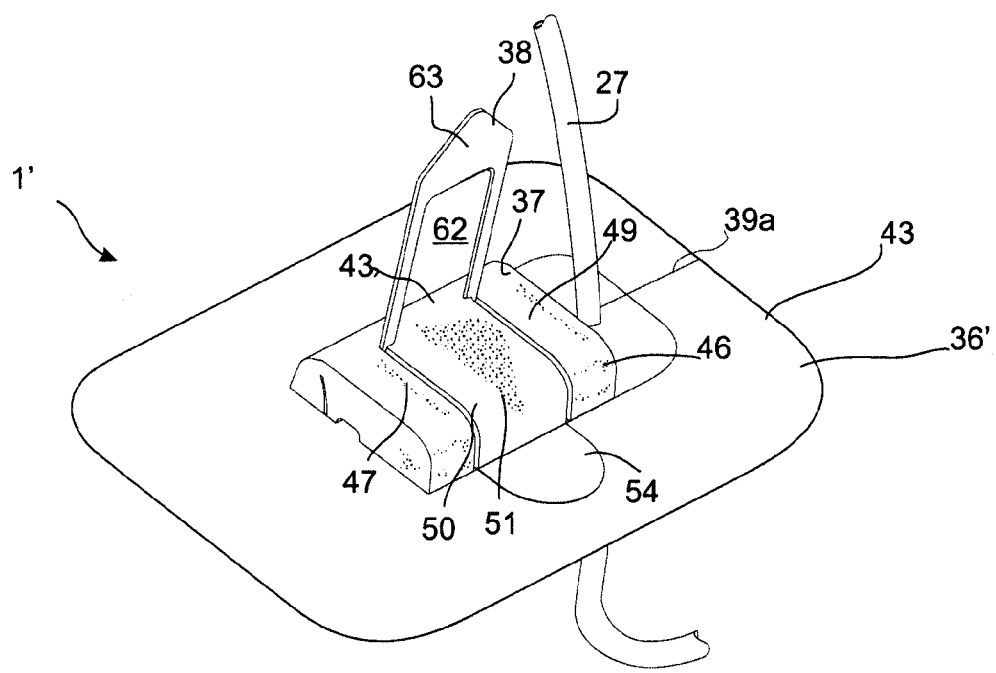
Figure 17:
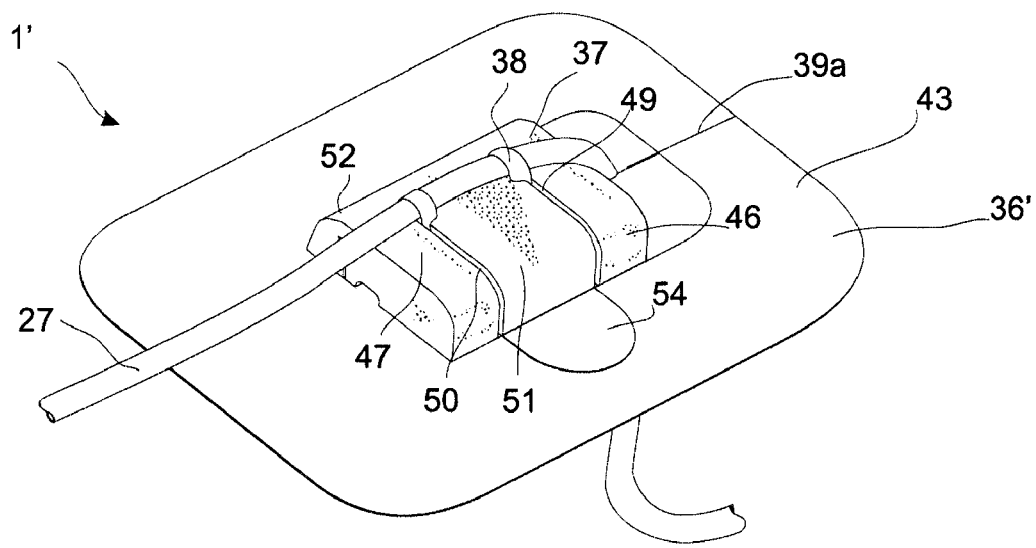
Figure 18:
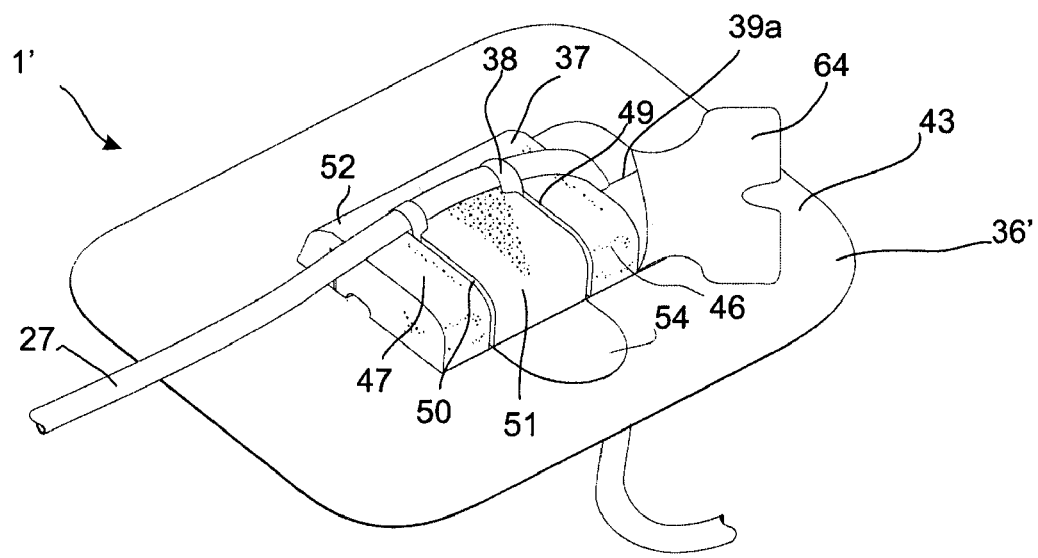

FIG. 14 is a perspective exploded view of the elements of a third embodiment of a plaster device according to the present invention, FIG. 15 shows the third embodiment in an assembled state where the fastening flap is assembled, FIG. 16 shows the third embodiment with a tube inserted and the release liner removed, FIG. 17 shows the third embodiment where the fastening flap is bent and secured on top of the support part, and FIG. 18 shows a modified third embodiment which includes a cover flap for covering the tube.

DETAILED DESCRIPTION OF THE PREFERRED EMBODIMENTS

A short length of the medical tube is shown in the figures for illustrative purposes only.

Also, the adhesive part is shown to be rectangular, however other geometrical outlines such as e.g. oval or circular are also within the scope of the present invention.

The area of the adhesive part exceeds the base area of the support part, and the adhesive part's through-opening for the tube is located at a distance from the perimeter of the adhesive part in order to provide space for the joining of the cover parts.

The elements of the plaster device 1 are shown in the exploded view of FIG. 1. The plaster device is composed of four main elements: an adhesive part 2, a fastening means 3, a support part 4 and a cover part 5.

The adhesive part 2 has an upper side 6 and an adherent bottom side 7, the adhesive of which is protected with a detachable sheet of protective foil 8. The adhesive part 2 has a slit 9 extending a distance from the perimeter 10 of the adhesive part 2 into said adhesive part 2 for meeting a through-opening 11 for the tube 27 in the use-position shown in FIGS. 3-6.

The fastening means 3 is an elastic band 3 having a circular cross-section. However, other cross-sections such as rectangular or quadratic may be preferred for some uses, since they may provide a better friction against the tube's outer surface.

The fastening means 3 is interposed between the adhesive part 2 and the support part 4.

Said support part 4 has a convexly curved upper supporting surface 12 for supporting the tube in the use-position and an underside 13.

The support part 4 is divided into a front-end part 14, a rear-end part 15, and a central portion 16 by means of two opposite facing recesses 17,18. The recesses branch-off from the support part the central, cleat-shaped portion 16 with two diametrically opposite arms 19,20. The central portion 16 is integral with the front-end part 14 and the rear-end part 15 at a longitudinal central section 21 along the longitudinal centre axis A of the support part 4. The front-end part 14 is attached to the upper side 6 of the adhesive part 2 adjacent the through-opening 11. The rear-end part 15 is similarly attached to the adhesive part 2 distal from the through-opening 11 so that a channel 22, extending between the parallel sides 23,24, is created below the central portion 16.

The cover part 5 consists of a first cover part 5a and a second cover part 5b. The first cover part 5a is, in the embodiment shown in the figures, a rectangular Velcro® sheet having substantially the same or slightly greater area as compared to the adhesive part 2.

The adhesive part is preferably made of a transparent material allowing inspection of the skin surface underneath it. In this case the second cover part 5b must not cover the entire adhesive part 2. Hence, the second cover part 5b is preferably a rectangular strip 5b, also made of Velcro®. The narrow Velcro® strip 5b is attached along the perimeter 10 of the adhesive part 2 on the outer rim portion of said adhesive part 2 e.g. by means of an adhesive and faces the first cover part 5a. The ends of the strip 5b meet at opposite facing sides of the slit 9. Due to the narrow width of the second cover part 5b, a central area of the adhesive part 2 remains uncovered. Inspection of the underlying skin surface is therefore still possible.

The cover parts 5a,5b can firmly and detachable be joined together by velcroing. The cover parts 5a,5b can have other types of adherent or sticky contact areas, such as e.g. glued contact areas covered by protective peelable foils. However, these alternatives are less preferred since such joinings are difficult to break and re-establish without damaging the adhesiveness of the cover parts 5a,5b or risking that the adhesive part 2 detaches from the skin surface to which the device 1 is attached.

The first cover part 5a has a cover part slit 25, which extends a distance from the perimeter 26 of the cover part 5a into said cover part 5a. The slit 25 defines two opposite facing flaps 30,31 which together with the slit 25 serve for guiding the bent length of the tube 27 and for holding the tube 27 substantially parallel with the subjacent skin surface (not shown).

FIG. 2 shows the plaster device 1 according to the invention with the through opening 11 of the plaster device 1 located around the tube 27.

The protective foil 9 is shown partly detached from the adherent bottom side 7 of the adhesive part 2. A substantially flat narrow elastic band 3 is placed in the channel 21 between the support part 4 and the adhesive part 2 and passed into opposite recesses 17,18 and around the arms 19,20, thereby forming two fastening loops 28,29.

As best seen in FIG. 3 the tube 27 is bent into a right angle until the tube rests firmly on the convexly curved upper supporting surface 12 of the support part 4.

The change of angle of the inserted tube 27 takes place when the tube is bent from a first position in which the tube is inserted via the incision site substantially perpendicular to the patient's skin, to a second position substantially parallel to the patient's skin, in which the bent length of the tube rest on the convexly curved upper supporting surface 12 of the longitudinal central top section 21 of the support part 4.

In FIG. 3 the fastening loop 28 has already been passed across the tube 27 and is situated in the recess 18 securely around the arm 20. Laterally reverse of the fastening loop 28, the fastening loop 29 is shown in the process of crossing in over the tube 27 for being situated in the opposite recess 17 in a manner corresponding to the one for the fastening loop 28.

As illustrated in FIG. 4 both the elastic fastening loops 28,29 are now situated around the arms 20,19 in respective opposite recesses 18,17, and the bent length of the tube 27 is firmly anchored by the crossed fastenings loops on the upper supporting surface 12 of the support part 4. Due to the chosen elasticity of the fastening means, the lumen of the tube is never squeezed. A frictional force between the tube and the fastening means guarantees that the tube is prevented from moving or displacing. No stitches at the incision site or grooves or depressions in the support part are required for holding the tube in place. However, such means can be used if considered expedient.

At seen better in FIG. 5 the convex shape of the upper supporting surface 12 provides a smooth anti-kinking support and guidance for the tube 27, which is bended via a right angle from a position substantially perpendicular to the patient's skin to the position substantially parallel to the patient's skin. The fastening means 3 passes through the channel 22, and extends into the crossed fastening loops 28,29.

FIG. 6 shows a section along the line VI-VI in FIG. 4 and illustrates how the fastening loops 28,29 passes in the channel 22 underneath the support part 4.

FIG. 6 demonstrates that the support part is an integral unit along the central part 16 of the support part 4, and FIG. 7 demonstrates the transverse integrity of the support part.

FIG. 8 shows a preferred way of fastening the fastening means 3. The fastening means 3 is before use arranged as shown and described for FIG. 2. Now, instead of crossing over the fastening loops 29,28 for fastening around respective opposite arms 19,18 only one of the loops is crossed over the tube.

Hence, by pulling the fastening loop 29 for anchoring around the opposite arm 19 the other fastening loop 28 is tightened around it's adjacent arm 19 on the central portion 16 of the support part 4 substantially parallel to the tube 27. This way of fastening prevents the arms 18,19 from being lifted up above the tube 27 in the resting position of the tube 27 on the longitudinal central section 21.

In FIG. 9 the first cover parts 5*a* are finally arranged over the supported tube and velcroed to the second cover part 5*b* for fully enclosing the supported tube.

The tube is exteriorised from the first cover part 5*a* via the slit 25 and the flaps 30,31 are arranged underneath the exteriorised part of the tube and velcroed to the second cover part 5*b*.

The first cover part 5*a* can easily be detached from the second cover part 5*b* in case inspection is needed. For example cleaning around the tube may be needed if leakage occurs around the tube or bleeding sets in at the incision site.

FIGS. 10 and 11 illustrate a second embodiment 32 for a plaster device according to the present invention. This plaster device 32 corresponds substantially to the first embodiment 1 and for like part are used same reference numbers.

The plaster device 32 has an annular second cover part 33*b* surrounding the support part 4 but covering an area smaller than the area of the adhesive part 2.

In FIG. 11 the first cover part 33*a* is velcroed together with the second cover part 33*b* to enclose the support part 4 and the bended length of the tube. The second cover part has a smaller size than the size of the adhesive part to leave the outmost edge zone 34 of the adhesive part 2 free of covering to provide an edge zone 34 of resistance to drawing and movement forces and allow the plaster device 32 to maintain its firm adhesive attachment on the skin. This plaster device 32 provides optimum attachment conditions and a minimum risk of detachment when the wearer moves around.

FIG. 12 shows a third, very simple embodiment of a plaster device 35 according to the present invention. The plaster device 35 is comprised of the support part 4 and a fastening means 3 for securing a bent length of a tube inserted in a body of an individual (not shown), as described for the first and second embodiment of a plaster device according to the present invention, and for like part are used same reference numbers. The plaster device 35 has an adhesive 36 on the underside 13 facing opposite the convexly curved upper supporting surface 12 of the support part 4. As soon as the plaster device 35 is arranged on top of the skin surface adjacent the tube inserted into the opening in the patient the plaster device 35 functions just as the support part 4, as described above for the first and second embodiments of plaster devices 1; 32.

As seen best in the cross-sectional view of FIG. 13 a channel 22, is created below the central portion 16 to provide accommodation for the fastening means 3. However, within the scope of the present invention adhesive may be provided on the underside 13 to an extent in which both the underside 13 of the support part 4 and the fastening means are entirely or partly adhered to the surface to which the plaster device are to be attached.

FIG. 14 shows an exploded view of the elements of a third embodiment for a plaster device 1'. The plaster device 1' has an adhesive part 36', a support part 37, and a fastening means 38. The third embodiment 37 has a support part being only half the previous embodiments of supports part, in that the cleat has only one arm.

The adhesive part 36' has a first adhesive transparent film member 39 with an upper side 40 and an adherent bottom side 41, the skin friendly-adhesive of which is protected with a detachable sheet, in the case shown a release liner with three release liner flaps 42*a*,42*b*,42*c*. The first adhesive member 39 has a slit 39*a* extending a distance from the perimeter of the adhesive member 39 into said adhesive part 36' to provide access for a tube (not shown) in the use-position in a manner similar as described for FIGS. 3-6. A second adhesive member 43, having a larger outline than the first adhesive member 39, is adhered to the upper side of the first adhesive member 39, leaving an adhesive circumferential rim zone 44 free to also be protected by the release liner flaps 42*a*,42*b*,42*c*. The second adhesive member 43 has a window 45 covered by the first adhesive member 39 to improve visibility at the incision site and allow for application of the plaster device 1' in and at the correct position. The release liners 42*a*,42*b*,42*c* may expediently be of larger area than the adhesive members 39,43 to leave a grasping edge 45 free. The second adhesive member 43 has a slit 43*a* to be aligned with the slit 39*a* of the first adhesive member 39 to be able to in combination open the slits 39*a*,43*a* to allow space for the inserted tube.

The support part 37 is divided into a front-end part 46, a rear-end part 47, and a central portion 48 by means of two opposite facing slots 49,50 crosswise the direction B intended for bending the tube. The slots 49,50 branch-off from the support part 37 a central, cleat-shaped portion 48 in the form of a fastening flap 51 pivotably hinged between the front-end part 46 and the rear-end part 47 by means of the remaining goods 52 of the support part 37 opposite the free end 53 of the fastening flap 51, which remaining part of the goods 52 serves as a hinge 52 making the fastening flap 51 pivotable between said front-end part 46 and said rear-end part 47. The space 56 between the front-end part 46 and the rear-end part 47 serves for accommodation of, among other things, the fastening flap 51. The fastening flap 51 has a first face 54 onto which the bent length of a tube is to rest. A second face 55 opposite the first face 54 is provided with a second engagement means 57 to engage a first engagement means 58 on the adhesive part arranged in the space 56. The second engagement means 57 has a finger grasping flap 59 of a material that is flexible and does not get stuck on other elements exterior to the plaster device or to the plaster device itself. Preferably the first and second mating engagement means are made as hook and loop fasteners.

As will be more clear from the following figures the second face 55 of the fastening flap 51 has an attachment means 60, in the form of a groove 60 for attachment of a first part 61 of the fastening means 38. In the third embodiment 1' a suitable fastening means 38 is a flat elastic rubber loop 38 having an rectangular outline to better fit securely into the groove 60 when the fastening flap is ready for use inside the loop opening 62. The rubber material provides a high degree of friction against the tube's outer surface and prevent displacement of the tube once the tube has been inserted in the body. The second end 63 of the fastening means 38 is intended to be grasped by the user, pulled over the tube resting on the fastening flap 51, and elastically extended in order to pass the loop opening 62 over the free end 53 of the fastening flap 51, subsequent to which the elastic fastening means 38 is allowed to relax. Thus the fastening means 51 is let loose at the second face 55 of said fastening flap 51 whereby the fastening means 51 conforms around the fastening flap 51 and the tube resting on the first face 54 of the fastening flap 51 to hold the tube firmly in frictional engagement on top of the support part 37.

Thus the fastening means 38 is interposed in the space 56 between the adhesive part 36' and the front-end part 46 and the rear-end part 47 of the support part 37 and neither the tube nor the fastening means can displace once the engagement means has been mated to engage each other.

FIG. 15 shows the third embodiment 1' in assembled state with the ears of the release liner flaps 42*a*,42*c* slightly bend away from the adhesive member 39. The fastening flap 51 is arranged in the space 56 between the front-end part 46 and the rear end part 47, the first end 61 of the fastening means 38 is arranged in the attachment groove 60 so that the second end 63 of the fastening means 38 protrudes outside the support part 37.

In FIG. 16 the release liner has been removed from the adherent bottom side 41 of the adhesive members 39,43 and a tube 27 has been inserted through the slits 39a,43a. As shown in FIG. 17 the tube 27 is bent to rest on top of the support part 37, first on top of the front-end part 46, further on the first face 54 of the fastening flap 51, and leaves the support part 37 via the rear-end part 47. The second end 63 of the fastening means 38 has been pulled to the second face 55 of the fastening flap 38 by pulling the opening 62 of the fastening means 38 over the free end 53 of the fastening flap 51, while the fastening flap is in the open pivoted position shown in FIG. 14.

Subsequently, as shown in FIG. 17 the fastening flap 51 has been pivoted into the space 56 and the first engagement means 58 is engaged with the second engagement means 57. During manipulation of the fastening means 38 the first end 61 of said fastening means 38 is firmly located inside the groove 60 to avoid that the fastening means 38 accidentally gets loose of its securing on the support part 37, which securing is necessary when moving the loop opening 62 over the fastening flap 51.

FIG. 18 shows a modification 1" of the third embodiment shown in FIGS. 14-17. The modified third embodiment 1" differs only in that the plaster device 1" further has a cover flap 64 for covering the tube 27 at least on the front-end part 46. The cover flap 64 may be preliminarily partly adhered to the adhesive member 36' and protected by a detachable release liner (not shown). Alternatively a cover means corresponding to the cover means used in the preceding embodiments can be used.

Yet a further beneficial feature is to provide a small area of the first face 54 of the fastening means 51 with an adhesive so that the tube 27 is better held in place on said first face 54 when the fastening means 38 is secured, without the tube slides off the support part.

Combinations of the above embodiments and features of the embodiments are foreseen within the scope of the present invention.

What is claimed is:

1. A plaster device for fixating a length of a medical tube in relation to a skin surface of an individual having the tube inserted into a body part via an opening, the device comprising:
   an adhesive part having an upper side, an adherent lower side for attaching the plaster device to the skin, and a through-opening for receiving the tube,
   a support part partly attached to the upper side of the adhesive part and arranged for supporting a bent length of said inserted tube, and
   fastening means for securing the tube on the support part,
   wherein the support part is an integral unit comprising a central part that is a pivotable fastening flap for attaching the fastening means,
   the pivotable fastening flap protrudes towards a free end between a front-end part of the support part and a rear-end part of the support part crosswise a longitudinal axis of the support part along which the bent length of the inserted tube extends when supported,
   the pivotable fastening flap is parted from the support part by means of at least two slots or incisions extending crosswise the longitudinal axis of the support part from a first side of the support part and by a distance towards a second side of the support part opposite the first side, and the bent length of the tube extends over the fastening flap, and the fastening means secures the tube to the fastening flap to prevent movement or displacement of the tube during use.

2. The plaster device according claim 1, wherein the plaster device further comprises cover means for covering at least a part of the bent length of the tube at least in the vicinity of the through-opening.

3. The plaster device according to claim 2, wherein the cover means includes a first cover part arranged for coupling together with either a second cover part attached to at least a section of the upper side of the adhesive part or for coupling to the adhesive part itself.

4. The plaster device according to claim 3, wherein the first cover part is an at least partly detachable textile sheet, either entirely made of hook and loop material or is provided with a strip of hook and loop material along the perimeter, and of an area sufficiently large to cover at least the support part in the use position, and the second cover part is an annular strip of hook and loop material attached to the upper side of the adhesive part.

5. The plaster device according to claim 3, wherein the cover means is an adhesive film.

6. The plaster device according to claim 3, wherein the cover means is transparent.

7. The plaster device according to claim 1, wherein the fastening flap has a first face for supporting the bent length of the inserted tube, and an opposite second face, said second face has attachment means for attaching at least a first part of the fastening means leaving a second part of the fastening means accessible.

8. The plaster device according to claim 7, wherein that the attachment means is a groove or hook.

9. The plaster device according to claim 1, wherein at least an area of the support part supporting the bent length of the tube has a retainer means for retaining the tube.

10. The plaster device according to claim 9, wherein the fastening flap incorporates the retainer means.

11. A method of applying the device of claim 1 to a subject, which method comprises:
    applying the plaster device on the subject with the tube in proximity to the front-end part of the support part,
    bending the tube in supported relationship on the support part,
    folding the second part of the fastening means over the bended length of the tube; and
    securing the second end of the fastening means on the second side of the fastening flap.

12. The method according to claim 11 which further comprises applying cover means to at least cover the bent length of the tube in proximity of the through-opening.

13. The plaster device according to claim 1, wherein the fastening means is made of elastic, flexible, resilient or springy material.

14. The plaster device according to claim 1, wherein the fastening means is a ring, loop, band or strip of rubber, silicone or polyurethane.

15. The plaster device according to claim 1, wherein the fastening flap has a free end as a grasping flap.

16. The plaster device according to claim 1, wherein at least an area of the upper side of the adhesive part between the front-end part and the rear-end part of the support part has a first engaging means and the second side of the fastening flap has a second engaging means for releasable engaging the first engagement means.

17. The plaster device according to claim 1, which further comprises at least one of an absorbent agent, a bactericide, a fungicide or a medicament.

18. The plaster device according to claim 1, wherein the adhesive part has a slit extending from the outer perimeter of the adhesive part to the through-opening.

19. The plaster device according to claim 1, wherein the adherent lower side of the adhesive part for attaching the plaster device to the skin is protected by at least one release liner.

20. A plaster device for fixating a length of a medical tube in relation to a skin surface of an individual having the tube inserted into a body part via an opening, the device comprising:

an adhesive part having an upper side, an adherent lower side for attaching the plaster device to the skin, and a through-opening for receiving the tube, a support part partly attached to the upper side of the adhesive part and arranged for supporting a bent length of said inserted tube, and fastening means for securing the tube on the support part, wherein the support part is an integral unit comprising a central part that is a pivotable fastening flap for attaching the fastening means, the pivotable fastening flap protrudes towards a free end between a front-end part of the support part and a rear-end part of the support part crosswise a longitudinal axis of the support part along which the bent length of the inserted tube extends when supported, the pivotable fastening flap is parted from the support part by means of at least two slots or incisions extending crosswise the longitudinal axis of the support part from a first side of the support part and by a distance towards a second side of the support part opposite the first side, and the fastening means is detachably arranged in relation to the support part and the adhesive part.

21. A plaster device for fixating a length of a medical tube in relation to a skin surface of an individual having the tube inserted into a body part via an opening, the device comprising:

an adhesive part having an upper side, an adherent lower side for attaching the plaster device to the skin, and a through-opening for receiving the tube, a support part partly attached to the upper side of the adhesive part and arranged for supporting a bent length of said inserted tube, and fastening means for securing the tube on the support part, wherein the support part is an integral unit comprising a central part that is a pivotable fastening flap for attaching the fastening means, the pivotable fastening flap protrudes towards a free end between a front-end part of the support part and a rear-end part of the support part crosswise a longitudinal axis of the support part along which the bent length of the inserted tube extends when supported, the pivotable fastening flap is parted from the support part by means of at least two slots or incisions extending crosswise the longitudinal axis of the support part from a first side of the support part and by a distance towards a second side of the support part opposite the first side, at least an area of the support part supporting the bent length of the tube has a retainer means for retaining the tube, and the retainer means is an adhesive.

\* \* \* \* \*